(12) United States Patent
Quigley et al.

(10) Patent No.: US 11,114,192 B2
(45) Date of Patent: Sep. 7, 2021

(54) DATA PROCESSING SYSTEM FOR PROCESSING NETWORK DATA RECORDS TRANSMITTED FROM REMOTE, DISTRIBUTED TERMINAL DEVICES

(71) Applicant: Sidecar Health, Inc., El Segundo, CA (US)

(72) Inventors: Patrick Quigley, Palos Verdes Estates, CA (US); Veronica Osetinsky, Belmont, CA (US); Shelby Moulden, Long Beach, CA (US)

(73) Assignee: Sidecar Health, Inc., El Segundo, CA (US)

( * ) Notice: Subject to any disclaimer, the term of this patent is extended or adjusted under 35 U.S.C. 154(b) by 0 days.

(21) Appl. No.: 16/655,982

(22) Filed: Oct. 17, 2019

(65) Prior Publication Data
US 2020/0126652 A1  Apr. 23, 2020

Related U.S. Application Data

(60) Provisional application No. 62/746,747, filed on Oct. 17, 2018.

(51) Int. Cl.
*G16H 20/10* (2018.01)
*G06Q 20/26* (2012.01)
*G06Q 40/08* (2012.01)

(52) U.S. Cl.
CPC ............ *G16H 20/10* (2018.01); *G06Q 20/26* (2013.01); *G06Q 40/08* (2013.01)

(58) Field of Classification Search
CPC ......... G16H 20/10; G16Q 20/26; G16Q 40/08
See application file for complete search history.

(56) References Cited

U.S. PATENT DOCUMENTS

| | | | |
|---|---|---|---|
| 2005/0055251 A1* | 3/2005 | Ashley | G06Q 40/08 705/4 |
| 2005/0114173 A1 | 5/2005 | Harris | |
| 2007/0050210 A1 | 3/2007 | Wiley | |
| 2007/0162308 A1* | 7/2007 | Peters | G16H 10/60 705/2 |
| 2011/0071854 A1 | 3/2011 | Medeiros et al. | |
| 2013/0117033 A1 | 5/2013 | Mohlenbrock | |
| 2014/0006050 A1* | 1/2014 | Feinschreiber | G06Q 40/06 705/2 |
| 2016/0300025 A1 | 10/2016 | Grossman et al. | |

FOREIGN PATENT DOCUMENTS

| AU | 2014200287 | 2/2014 |
|---|---|---|
| CA | 2659781 | 12/2008 |

OTHER PUBLICATIONS

PCT International Search Report and Written Opinion in International Appln. No. PCT/US119/56752, dated Jan. 13, 2020, 8 pages.

* cited by examiner

*Primary Examiner* — Scott C Anderson
(74) *Attorney, Agent, or Firm* — Fish & Richardson P.C.

(57) ABSTRACT

Disclosed is a computing architecture and method for operating and managing a health care plan from a mobile device or web browser. The present invention provides an architecture that facilitates customer access to affordable, personalized health care, along with the efficient processing of claims.

24 Claims, 14 Drawing Sheets

2175 Hyde Place

Diagnoses

Influenza due to certain identified influenza viruses
W56.49XA

Procedures

| CARE RECEIVED | PROVIDER RATE | SIDECAR COVERS |
|---|---|---|
| First-time doctor visit 99203 | $145.00 | $120.00 |
| ● 5 price modifiers | | |
| Flu test 87804 | $6.99 | $10.00 |
| ● 1 price modifier | | |
| Total | $151.99 | $130.00 |

1000

```
Receive, over a payment processing network, a request requesting
payment for a health care service
                                                              1002
```

```
Process, in near real time through a payment network, cash payment
of the health care service
                                                              1004
```

```
Access, from a hardware storage device, a node labeled with the key
                                                              1006
```

```
Look up, in the accessed node, coverage data
                                                              1008
```

DATA PROCESSING SYSTEM FOR PROCESSING NETWORK DATA RECORDS TRANSMITTED FROM REMOTE, DISTRIBUTED TERMINAL DEVICES

CLAIM OF PRIORITY

This application claims priority under 35 U.S.C. § 119(e) to U.S. Provisional Application Ser. No. 62/746,747, filed Oct. 17, 2018, the entire contents of which are hereby incorporated by reference.

TECHNICAL FIELD

The techniques described herein generally pertain to a data processing apparatus for processing network data records transmitted from a plurality of remote, distributed terminal devices.

BACKGROUND

Computer systems can be used to transmit, receive, and/or process data. For instance, a server computer system can be used to receive and store resources (e.g., payment data), and make the content available to one or more client computer systems. Upon receiving a request for the content from a client computer system, the server computer system can retrieve the requested content, and transmit the content to the client computer system to fulfill the request.

SUMMARY

The data processing system allows a consumer to pay a cash rate cost for a health care service. A consumer can purchase a health care service and receive an insurance benefit using a payment card associated with the consumer's account. The card can include a credit or debit card. This enables a consumer to purchase health care services and receive insurance benefit as if the health care service were any product being purchased with a credit or debit card, where the benefit is applied at the time of purchase at the point of sale device. The health care service provider experiences the purchase as if the purchase were with cash (e.g., cash, credit, or other form of non-insurance payment). The consumer receives the benefit amount according to that consumer's coverage plan at the time of purchase. Often, purchasing the health care service with cash results in a lower price for the consumer. The data processing system allows the consumer to take advantage of this reduced, cash rate cost while also having insurance benefit pay at least a portion (or substantially all) of the cost.

The methods of payment and claims by the data processing system provides a simpler alternative to traditional insurance payments and claims processing. In the traditional method, a consumer provides their insurance card at the time of receiving a health care service. After the health care service is received, the health care service provider transmits an invoice, which includes a negotiated cost of the health care service with the particular insurance provider, rather than a cash rate cost. The insurance company remits payment based on a coverage plan for that consumer and sends a bill to the consumer for the remaining balance of the cost which consumer is then responsible for completing payment, often weeks or months after receiving the health care service.

The data processing system enables the removal of the health insurance company as a middleman between the consumer and the health care service provider for the transaction. Instead, each consumer can pay with a charge card, credit card, or other form of account identifier that identifies the consumer to the point of sale device. Based on the identification of the consumer's account with the purchase (e.g., because the card or other payment device is linked to the consumer's insurance account in the data processing system), the data processing system immediately satisfies the cost, and the health care service is paid in full. Because this is preferable to the health care service provider, the health care service provider often offers the health care service at a lower cost if cash is received immediately. The consumer's account receives the charge, a fixed benefit amount (based on the cash rate cost) is deduced from the cost, and the difference is credited/debited to the consumer's payment account, either directly or indirectly. If the consumer does not have a direct payment account in the data processing system, the data processing system prompts the consumer to send representation of the bill for the health care service for verification of the cost paid. For example, the consumer can take one or more photos of the receipt from the doctor/medical facility, attach the photo(s) to the expense, and submit the expense to a claims team, all through a user interface. In some implementations, the consumer, having already provided a personal credit card or bank account number when signing up for a plan, is automatically charged for their portion of medical costs. Most payments can be resolved within twenty-four (24) hours.

A user interface of the data processing system can display various data to the consumer. For example, because the cash rate cost is determined for each health care service, the data processing system is capable of displaying to a consumer exactly how much of a benefit amount is provided for each health care service the consumer uses. In another example, as stated above, through the user interface, the consumer can set a coverage level using an application on a device of the consumer (e.g., during enrollment in an insurance plan). The application shows the consumer, though the user interface, how much each health care service costs, how much coverage costs, and what the benefit is for each health care service.

Other benefits are also possible. Consumers can use a smartphone application or a web-based application to determine the coverage amount their plan will pay toward a health care service before they see the doctor. They ask the doctor for the cash price of the service, take into consideration the amount their plan will cover, and therefore know the amount they will have to pay out of pocket before obtaining the health care service.

In some implementations, to provide a better experience for consumers, the data processing system includes a self-pay data sharing system where users can add cash prices they paid at their medical visit. This method of crowdsourcing data is an efficient way to build a database of true cash prices that other consumers can refer to when choosing a doctor or medical facility.

The data processing system is able to satisfy the cost of the health care service in response to receiving the transaction data in real time or near real time in order to meet electronic payment timeout requirements (such as with credit or debit card transactions). The data processing system is configured to validate the transaction within this time window, ensuring that the purchase is covered by a consumer's insurance plan.

In an aspect, a data processing system is configured for providing a cash payment for a health care service that is at least partly covered by a health insurance provider over a payment processing network. The data processing system receives a request requesting payment for a health care service and a key that uniquely identifies a consumer of health care services; in near real-time with respect to when the request is received, processing, through a payment network, cash payment of the health care service; accessing, from a hardware storage device, a node labeled with the key; and looking-up, in the accessed node, coverage data that specifies an amount of the health care service paid by a health insurance provider of the payment network and an amount paid by the consumer, where the amount paid by the health insurance provider is a specified amount of a determined cash rate cost of the health care service regardless of a source of the health care service.

In some implementations, the data processing system determines the cash rate cost of the health care service by, for a plurality of requests requesting payment for instances of the health care service, determining a set of total costs including a total cost requested for each instance of the health care service; and applying a weighted average to the set of total costs. In some implementations, the request is received in response to a transaction by a payment card of the consumer. In some implementations, the actions include providing a user interface configured to present the coverage data or the determined cash rate cost for one or more health care services.

In an aspect, a data processing system is configured to process a payment for a health care service that is at least partly covered by a health insurance provider. The data processing system includes a data storage configured to store cash rate data representing cash rate costs paid for health care services for each of a plurality of transactions processed by point of sale systems of health care providers. The data processing system includes a payment processing engine configured to: receive transaction data indicating a purchase of a health care service at a point of sale system of a health care provider using a payment card identifying a consumer of the health care; in response to receiving the transaction data, access a profile of the consumer, the profile specifying a payment source for the purchase of the health care; retrieve co-pay data from the payment source, the co-pay data specifying a portion of a cost of the health care being paid by the payment source; cause, within a threshold time of receiving the transaction data, the portion of the cost to be satisfied from the payment source and a remaining portion of the cost to be satisfied from a coverage account; access the data storage to receive the cash rate data associated with the health care; determine a benefit amount of the cost of the health care, the benefit amount of the cost being based on the cash rate costs paid for the health care; determine a credit or a debit to apply to the payment source by comparing the benefit amount of the cost to the remaining portion of the cost satisfied by the coverage account; generate a notice of the credit or the debit; and cause transmission of the notice to a computing device associated with the consumer.

In some implementations, the payment processing engine is further configured to update the cash rate data associated with the health care in response to receiving the transaction data. In some implementations, the cash rate data comprises, for each health care, a weighted average of a cost for each instance of purchasing the health care in the plurality of transactions. In some implementations, the data storage comprises different cash rate data for each geographic region of a plurality of geographic regions associated with the plurality of transactions.

In some implementations, the benefit amount is adjusted based on one or more demographics of the consumer represented in the profile. In some implementations, the benefit amount is adjusted based on a cost coverage setting of the profile of the consumer. The transaction data comprises an identifier representing the health care service. In some implementations, the identifier can be mapped to various standard medical codes. In some implementations, receiving the transaction data comprises: requesting validation data for the point of sale system as being associated with an approved health care provider; and in response to receiving the validation data indicating that the health care is approved, enabling the remaining portion of the cost to be satisfied from the coverage account. In some implementations, causing, within the threshold time of receiving the transaction data, the portion of the cost to be satisfied from the payment source and the remaining portion of the cost to be satisfied from the coverage account, satisfies a timeout function of the point of sale system for the purchase of a health care.

In some implementations, the data processing system includes a user interface engine configured to generate presentation data for presenting the notice of the credit or the debit on the computing device associated with the consumer. The presentation data comprises a push notification or alert. The presentation data comprises the benefit amount for each transaction associated with the consumer. The presentation data is configured to be searchable based on the benefit amount.

In some implementations, the payment processing engine is configured to generate additional cost data representing a projected cost or credit associated with each of the plurality of transactions, the projected cost or credit being a function of the cash rate data for each of the transactions of the plurality; and where the presentation data comprises a representation of the additional cost data. In some implementations, determining the credit or the debit to apply to the payment source comprises: receiving image data representing a medical invoice including the cost for purchasing the health care service; extracting the cost from the image data; and verifying that the cost of the transaction data matches the extracted cost from the image data, where determining the credit or the debit to apply to the payment source comprises comparing the extracted cost to the benefit amount.

The details of one or more embodiments are set forth in the accompanying drawings and the description below. Other features and advantages will be apparent from the description and drawings, and from the claims.

BRIEF DESCRIPTION OF THE DRAWINGS

FIGS. 3-9 are examples of user interfaces.

DETAILED DESCRIPTION

Figure 1:
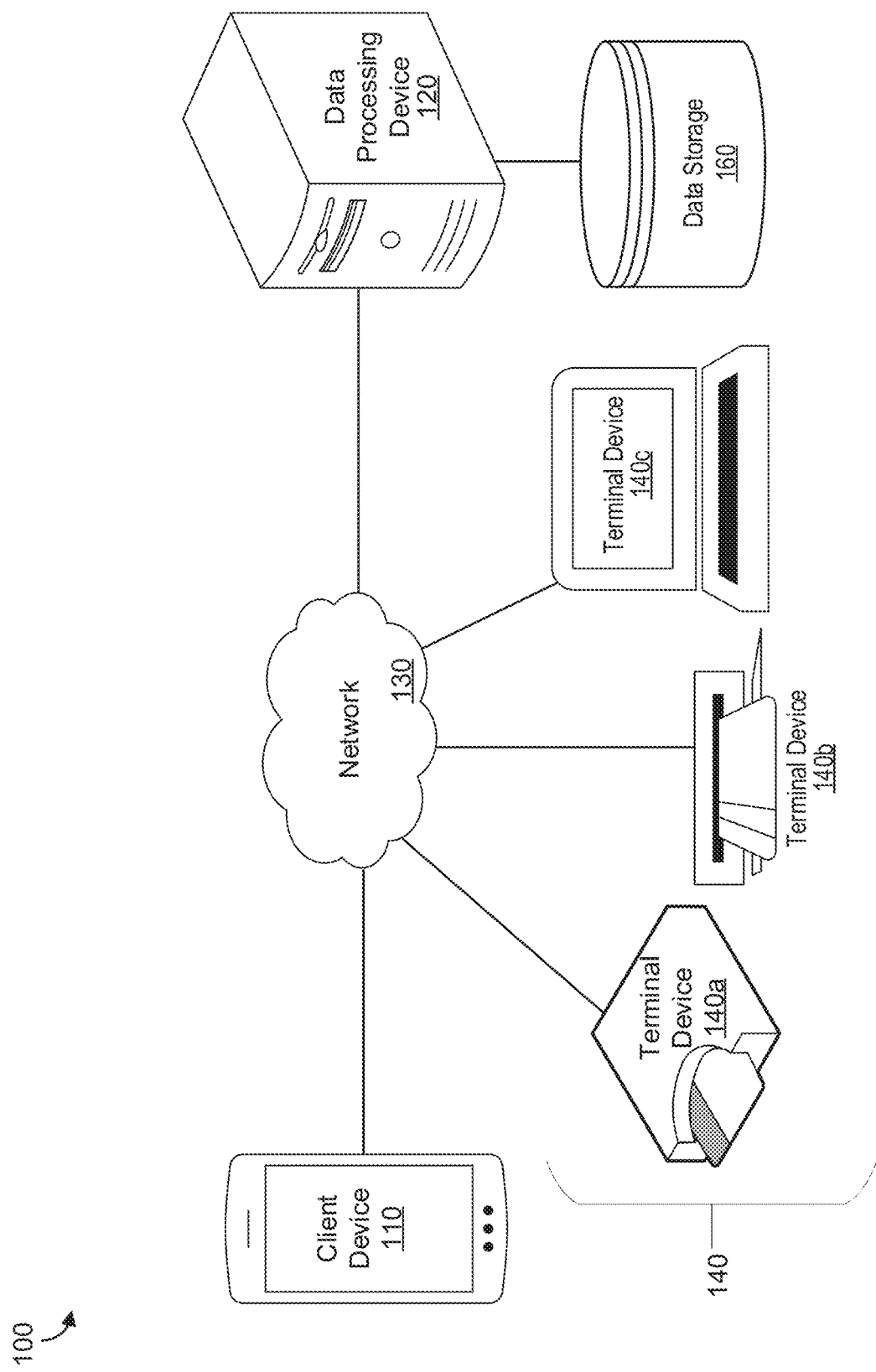
FIG. 1 is a block diagram of an example computing environment for processing network data records transmitted from a plurality of remote, distributed terminal devices.

The data processing system described in this document is configured for processing network data records transmitted from remote, distributed terminal devices. More specifically, the data processing system is configured to receive transaction data from a terminal device (e.g., a point of sale device) associated with a health care service provider and process the transaction data. Processing the transaction data includes determining which portions (e.g., amounts) of a cost, represented in the transaction data, for a health care service to be paid by each of a plurality of accounts associated with a consumer of the health care service. A health care service can include any health related product that can be purchased by a consumer, including doctor visits, prescription medication, medical device products, surgery, hospital visits, and so forth. The data processing system is configured to determine a first amount of the cost to be paid from an account of the consumer of the health care service and a second amount to be paid by an insurance provider associated with the consumer. The first and second amounts are based on the actual cash rate cost of the health care service being purchased. The cash rate cost of the health care service includes a fair market price of the health care service as determined by analysis of the market for the health care service, described in detail below. The data processing system is configured to compare the cost of the particular instance of the health care service being purchased to the cash rate cost. A benefit amount is determined based on coverage data for the consumer and the cash rate cost of the health care service. The data processing system is configured to respond to the transaction data by causing the cost to be satisfied within a threshold time period. The data processing system then determines a credit or debit amount, and generates notification data to send to a device of the consumer. The credit or debit amount is based on determining the difference between the amount of the cost that is satisfied in response to the transaction data and the associated benefit amount for that health care service. The benefit amount is also called a fixed indemnity amount.

The data processing system includes one or more of the following technical benefits. The benefit amount is determined by the data processing system based on the cash rate cost of the health care service. The data processing system is configured to process transaction data from a plurality of distributed terminal devices, such as point of sale devices. The data processing system determines, from the transaction data, the cash rate cost for each health care service. The data processing system presents data to a consumer, prior to receiving transaction data for a health care service for that particular consumer, an estimated cost of purchasing the particular instance of the health care service. Here, a health care service is a type of health care service, such as a prescription medication, surgery type, type of doctor visit, and so forth. An instance of the heath care service refers to a particular purchase of the health care service, such as visiting a particular doctor, buying a particular brand of a medication, visiting a particular hospital, and so forth. The cost of a first instance of a health care service can differ from the cost of another instance of the health care service, such as from a different provider such as a different doctor or hospital. The data processing system is configured to show the consumer what the cost of purchasing the instance of the health care service is to the particular consumer after the particular consumer's benefit is applied for receiving the health care service. Thus the consumer receives a transparent picture of the cost of each particular instance of each of a plurality of health care services.

FIG. 1 is a block diagram of an example computing environment 100 for processing network data records transmitted from a plurality of remote, distributed terminal devices 140. Generally, the data processing device 120 is configured to process transaction data from the terminal devices 140 and the client device 110. The environment shows an architecture for operating and managing health care plans. The data processing device 120 and client device 110 are configured to provide a personalized, comprehensive, fixed indemnity health insurance plan that allows the consumer to pay for medical services directly at the time of service at a cash rate cost. The data processing device 120 and client device 110 provide an architecture that facilitates access to health care plan information and claims processing from a single-point by the client device 110. The consumer purchases an insurance plan. Based on the coverage purchased and the cash rate cost of a health care service being purchased, a fixed benefit amount is applied to the purchase. The purchase is covered immediately at the point of sale as if the purchase were a cash purchase. The benefit amount is subsequently applied to the consumer's account, and based on the actual cost paid for the particular instance of the health care service, a credit or debit notice is sent to the client device 110 of the consumer.

The data processing device 120 is configured for processing network data records transmitted from remote, distributed terminal devices 140a, 140b, 140c (collectively terminal devices 140). While three terminal device are shown, in practice, hundreds, thousands, or tens of thousands of terminal devices 140 can transmit transaction data to the data processing device 120. More specifically, the data processing device 120 is configured to receive transaction data from a terminal device 140 (e.g., a point of sale device) associated with a health care service provider and process the transaction data.

Processing the transaction data includes determining which portions (e.g., amounts) of a cost, represented in the transaction data, for a health care service to be paid by each of a plurality of accounts associated with a consumer of the health care service. A health care service can include any health related product that can be purchased by a consumer, including doctor visits, prescription medication, medical device products, surgery, hospital visits, and so forth. The data processing device 120 is configured to determine a first amount of the cost to be paid from an account of the consumer of the health care service and a second amount to be paid by an insurance provider account associated with the consumer.

The first and second amounts are based on the actual cash rate cost of the health care service being purchased. The cash rate cost of the health care service includes a fair market price of the health care service as determined by analysis of the market for the health care service, described in detail below. The data processing device 120 is configured to compare the cost of the particular instance of the health care service being purchased to the cash rate cost. A benefit amount is determined based on coverage data for the consumer and the cash rate cost of the health care service. The data processing device 120 is configured to respond to the transaction data by causing the cost to be satisfied within a threshold time period. The data processing device 120 then determines a credit or debit amount, and generates notification data to send to a device of the consumer. The credit or debit amount is based on determining the difference between the amount of the cost that is satisfied in response to the transaction data and the associated benefit amount for that health care service. The benefit amount is also called a fixed indemnity amount.

The benefit amount is determined by data processing device 120 based on the cash rate cost of the health care service. For example, the benefit amount can be a percentage (e.g., 10%, 50%, 70%, 90%, 100%, etc.) of the determined cash rate cost of a health care service. The coverage level selected by a consumer can specify what the percentage of the cash rate cost is for the benefit amount. The benefit amount is fixed, regardless of the actual cost paid by the consumer or the health care service provider selected by the consumer. In other words, the same benefit amount is paid for a particular consumer for a health care service no matter how much the consumer pays for the health care service in a particular instance.

The data processing system is configured to process transaction data from a plurality of distributed terminal devices, such as point of sale devices. The data processing device 120 determines, from the transaction data, the cash rate cost for each health care service. The data processing device 120 presents data to a consumer (by the client device 110), prior to receiving transaction data for a health care service for that particular consumer, an estimated cost of purchasing the particular instance of the health care service. A health care service is a type of health care service, such as a prescription medication, surgery type, type of doctor visit, and so forth. An instance of the heath care service refers to a particular purchase of the health care service, such as visiting a particular doctor, buying a particular brand of medication, visiting a particular hospital, and so forth. The cost of a first instance of a health care service can differ from the cost of another instance of the health care service, such as from a different provider such as a different doctor or hospital. The data processing device 120 is configured to show the consumer what the cost of purchasing the instance of the health care service is to the particular consumer after the particular consumer's benefit is applied for receiving the health care service. Thus the consumer receives a transparent picture of the cost of each particular instance of each of a plurality of health care services. The consumer can set a coverage level, which determines a benefit amount for each health care service, in response to receiving this data.

The data processing device 120 allows a consumer to pay a cash rate cost for a health care service. A consumer can purchase a health care service and receive an insurance benefit using a payment card associated with the consumer's account. The card can include a credit or debit card. This enables a consumer to purchase health care services and receive insurance benefit as if the health care service were any product being purchased with a credit or debit card, where the benefit is applied at the time of purchase at the point of sale device. The health care service provider (which owns the terminal device 140) experiences the purchase as if the purchase were with cash (e.g., cash, credit, or other form of non-insurance payment). The consumer receives the benefit amount according to that consumer's coverage plan at the time of purchase. Often, purchasing the health care service with cash results in a lower price for the consumer. The data processing device 120 allows the consumer to take advantage of this reduced, cash rate cost while also having insurance benefit pay at least a portion (or substantially all) of the cost.

Generally, the data processing device 120 is associated with data storage 160. The data storage 160 can include any means for storing data, such as a database, mainframe, memory, etc. The data storage 160 is configured to store data records for each consumer associated with the data processing device 120. The data records represent at least portions of consumer profiles of consumers that have insurance accounts. A consumer profile includes data representing the consumer's coverage settings (e.g., an amount of coverage), a consumer identifier (e.g., a key value for the record), and, in some implementations, a payment account associated with the consumer. The consumer profile is described further in relation to FIG. 2.

The data processing device 120 is configured to communicate with the client device 110 over the network 130. The client device 110 can include most any computing device, such as described in relation to FIG. 12. Generally, the client device 110 includes a mobile computing device, such as a smart phone, or a desktop computing device, laptop, tablet, and so forth. The client device 110 is configured to present a user interface to the consumer. The user interface can show the consumer details about the consumer's account with the data processing device 120. The user interface can show the consumer what the cash rate cost is for various health care services, show the consumer the consumer's coverage setting, show an estimated out of pocket cost to the consumer for various health care services, and so forth. Example user interfaces as shown in relation to FIGS. 3-9.

The client device 110 allows the consumer to interact with the data processing device 120. The client device 110 allows, through the user interface, the consumer to set a coverage level for the consumer's insurance account. The client device 110 allows the consumer to specify a payment account from which to deduct funds for covering costs, such as co-pay costs and costs in excess of a benefit amount for a health care service. The client device 110 allows the consumer to send data to the data processing device 120, such as images of invoices for health care services purchased by the consumer. The data is communicated over network 130, which can include a communications network such as the Internet. Data exchanged by the devices of the environment 100 is described in relation to FIG. 2.

Generally, the consumer configures a consumer account with the data processing device 120 using the client device 110. The account includes an insurance plan that specifies a benefit amount for each of a plurality of health care services. The consumer pays an annual fee (or monthly tee, etc.) for having the insurance account. When the consumer purchases an instance of a health care service and identifies the account (e.g., with a payment card), the data processing device 120 receives the transaction data for the purchase and determines how much the insurance plan covers, while satisfying the cost in near real time by sending payment data to the terminal device 140 as if cash were being paid by the consumer associated with the account. This process is described in further detail with respect to FIG. 2.

Figure 2:
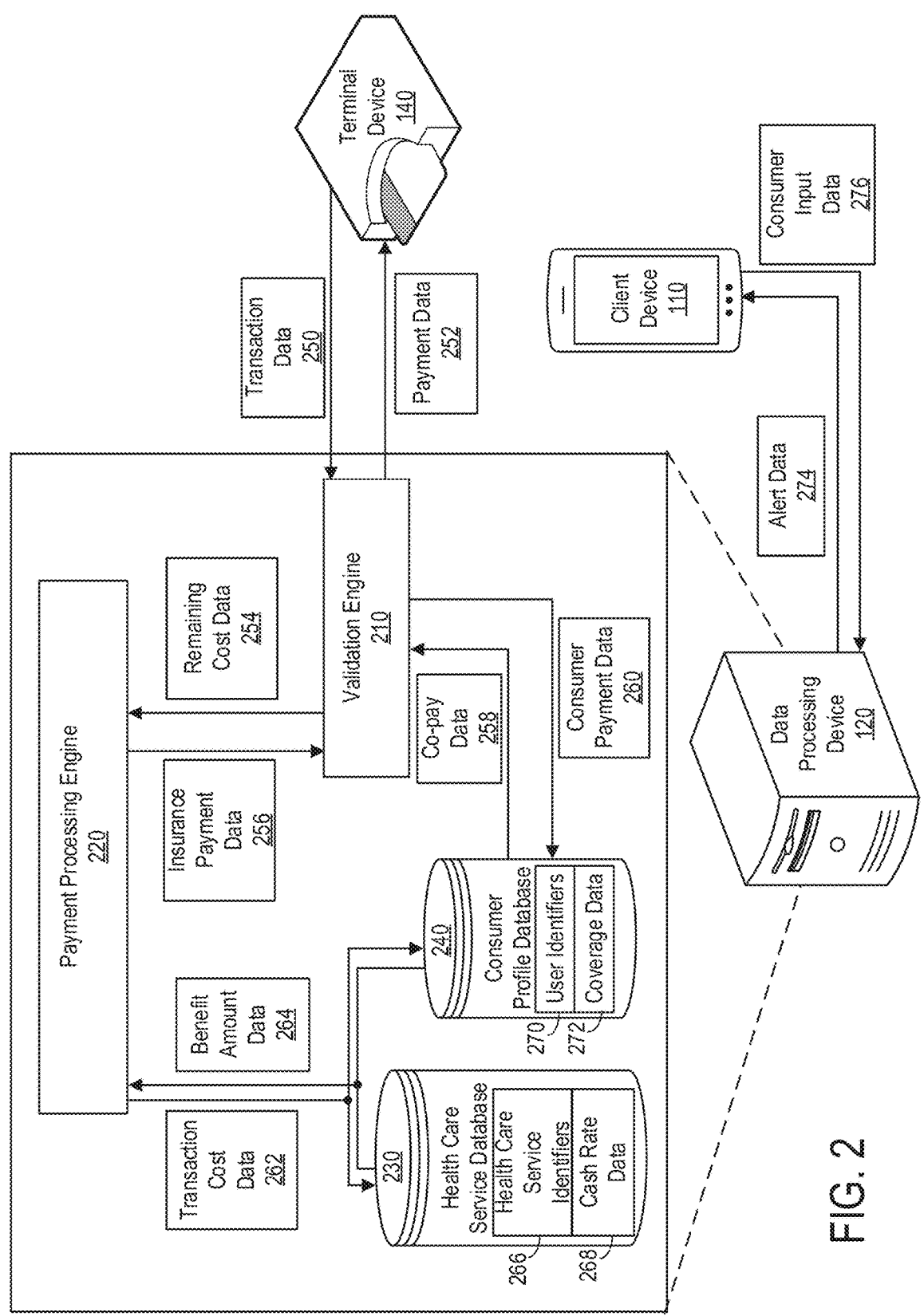
FIG. 2 is a block diagram of an example data processing system.

FIG. 2 is a block diagram 200 of an example data processing system including the data processing device 120, terminal device 140, and the client device 110. FIG. 2 shows data being communicated among the devices 110, 120, and 140 when a transaction occurs for which the consumer identifies his or her insurance account with the data processing device 120.

The consumer can purchase an instance of a health care service at the terminal device 140. The terminal device 140 generally includes a point-of-sale device, such as credit card reader or other such payment device. The consumer identifies his or her account when purchasing the health care service. The consumer can identify his account by using a payment card that includes the account identifier. For example, the payment card can be associated with the data processing device 120. When the card is activated, the transaction data 250 are sent to the data processing device 120. In some implementations, the consumer can identify his account by giving an account number to the health care service provider. The health care service provider can send the transaction data 250 to the data processing device 120.

Generally, the transaction data 250 includes a representation of a cost of the health care service to be paid by one or more accounts for completing the purchase. The transaction data 250 can also include an identifier identifying the account associated with the transaction (e.g., which consumer is making the purchase). In some implementations, the transaction data 250 includes an identifier that identifies the health care service being purchased.

The data processing device 120 is configured to process transaction data 250 received from the terminal device 140. For example, in response to a transaction occurring, the terminal device 140 send the transaction data 250 to the data processing device 120. The data processing device 120 processes the transaction data 250 to determine how much of the cost of the health care service is paid by each account associated with the consumer.

When the data processing device 120 receives the transaction data 250, the data processing device 120 can validate the purchase using a validation engine 210. The validation engine includes logic configured to determine whether the purchase is a valid purchase that should be paid by the consumer's account and the insurance account. For example, the validation engine 210 can determine that the health care service being purchased is being purchased from an approved terminal device 140. The validation engine 210 can check a list of approved vendors and determine whether the transaction data 250 is being received from an approved vendor before continuing to process the transaction data 250. In some implementations, the validation engine 210 can determine that the particular health care service identified in the transaction data 250 is an approved health care service that is covered by the consumer's insurance plan. In some implementations, the validation engine 210 can check an account of the identified consumer to ensure that the consumer is in good standing. For example, the validation engine 210 can confirm that the consumer has paid any premiums due, that debits of prior purchases are satisfied (or that arrears are below an acceptable threshold), and so forth.

If the validation finds that the consumer is in good standing, and that the health care service is an acceptable service from an approved health care service provider, the validation approves the purchase and the data processing device 120 proceeds to process the transaction data 250. If the health care service is not covered, or if the vendor is not approved, the data processing device 120 can reject the transaction. A message can be provided to the consumer (e.g., by the user interface of the client device) describing the reason why the purchase was rejected. The purchase is thus approved or rejected at the transaction data 250 at the point of sale of the service, rather than after the purchase has taken place. This reduces a likelihood that a consumer is surprised at a lack of coverage or other such issue after purchasing the health care service.

Once validated, the data processing system 250 processes the transaction data 250 to satisfy the purchase within a threshold amount of time to conform to payment system standards. For example, the data processing device 120 is configured to process the transaction data 250 and satisfy the purchase or reject the purchase within 50-500 milliseconds of receiving the transaction data 250.

The data processing device 120 determines what the co-pay of the purchase should be by the consumer. The validation engine 210 references a consumer identifier, which can be a part of consumer payment data 260 in the transaction data 250, in a consumer profile. The consumer profile is stored as a part of consumer profile data 240. The consumer's profile is accessed, and a co-pay amount is determined. This co-pay amount (a first amount) is covered by the consumer based on a coverage plan for the consumer. For example, if a consumer has maximum coverage, the consumer may never pay a co-pay, and the entire balance of the transaction is covered (initially) by the insurance account before the benefit amount is determined. The consumer profile data 240 includes a node labeled with a key. The key includes a user identifier of the consumer. The node includes the coverage data specifying the coverage level for the consumer, account data of the consumer (e.g., a personal account identifier and an insurance account identifier), and other data for the consumer profile.

The co-pay amount of the cost is paid directly from a payment account of the consumer. The payment account can be an account hosted by the data processing device 120, or the payment account can be a third party account that is charged by the data processing device 120 (such as a credit card account). The data processing device 120 receives the co-pay amount of the cost for satisfying the payment at the point of sale. The remaining cost is paid from an account of the insurance provider associated with the data processing device 120. The co-pay data 258 is sent back to the validation engine 210. When accepting the purchase, the validation engine 210 sends the account identifiers to the transaction data 250 identifying the accounts to debit for the co-pay and the remaining cost of the health care service. Thus, from the perspective of the health care service provider, the entire cost of the health care service is satisfied immediately as if the consumer were paying cash. In some implementations, the co-pay amount is determined by the payment processing engine 220. In some implementations, the payment processing engine 220 and the validation engine 210 are a combined logic engine configured to perform the functions of both the validation engine 210 and the payment processing engine 220.

Once the co-pay is deduced from the cost paid for the health care service by the consumer, the remaining cost data 254 is sent to the payment processing engine 220. The remaining cost data 254 includes the amount of the cost covered by the insurance account. If the co-pay amount is zero, then the remaining cost data 254 represents the entire cost of the health care service.

The payment processing engine 220 determines what the benefit amount is for the purchased health care service. The benefit amount represents the fixed indemnity benefit for the health care service. The benefit amount is determined based on coverage purchased by the consumer and based on the cash rate cost (also called the market cost) of the health care service. Because the health care service has already been paid for, the benefit amount need not be applied in near real time. While the benefit amount for a given health care service is known in advance of the purchase, the determination to apply the benefit amount to the consumer's purchase of an instance of the health care service need not be in near real time.

To apply the benefit amount to the purchase, the payment processing engine 220 sends transaction cost data 262 to a health care service database 230 and the consumer profile database 240. The health care service database 230 includes, for each health care service covered by the insurance plan of the consumer, a health care service identifier 266, and associated cash rate data 268 for that health care service.

The cash rate data 268 refers to the market cost of a health care service as determined by the data processing device 120. The cash rate data 268 generally refers to the cash cost of purchasing a health care service, rather than a negotiated cost between an insurance provider and a health care provider. The data processing device 120 is configured to simulate a cash payment for health care services from the perspective of the health care service providers, while also providing a fixed indemnity benefit amount to consumers that own the insurance plans. However, the cash payment need not be in actual cash—the payment can be using a payment card, credit card, debit card, etc. as described below. This can also be called a self-pay rate.

The data processing device 120 uses one or more methods to determine the cash rate data 268 for each covered health care service. The data processing device 120 can reference an existing rate paid by a large entity that represents the cost of buying the health care service in a market. For example, the cash rate for a health care service can be indexed to a cost paid by Medicare for a given health care service. In some implementations, the cost is a function of the cost paid by Medicare (e.g., a percentage). In some implementations, the cost is indexed to different values based on the geography of the market in which the health care service is being purchased (e.g., by state, county, city, country, etc.).

The cash rate data 268 can show a cash rate that is based on purchases actually made by consumers that are processed by the data processing device 120. For example, the data processing device 120 can track how much a health care service costs from different health care service providers in a region. The data processing device 120 can apply a weighted average (e.g., based on volume for a health care service provider for the service, reputation of a health care service provider, or some other factor) to the costs paid to represent the cash rate cost paid for the health care service. Similarly, the cash rate determined in this way can be segmented by geographical regions. The data processing device 120, by using the actual costs paid for many instances of a health care service, can determine with high accuracy what the cash rate for the health care service should be. Thus, the benefit amount can be tailored to the cash rates of the cash rate data 268 to provide consumers with high flexibility and transparency with regard to the amount of insurance they are purchasing in a plan and the resulting out of pocket costs for each health care service.

The payment processing engine 220 retrieves the cash rate data 268 from the health care service database 230. To determine the benefit amount data 264, the payment processing engine 220 determines the coverage level for the consumer for the purchase. The payment processing engine 220 retrieves the coverage data 272 associated with the user identifier 270 of the consumer.

The coverage data 272 specifies an amount of coverage purchased by the consumer represented by the user identifier 270 associated with the coverage data 272. The consumer can purchase a level of coverage based on how much of each purchase the consumer wants covered by the benefit amount. Generally, more coverage requires a higher premium. The consumer, by a user interface of the client device 110, can view what benefit amounts are to be paid for each health care service for each coverage level and set the coverage desired using controls of the user interface. Interactions with the user interface of the client device 110 generate consumer input data 276, which is sent to the data processing device 120 for processing. In some implementations, the consumer can set coverage on a per-health care service basis. In some implementations, the consumer sets an overall coverage level, such as low, medium, high, etc. The benefit amounts and premium costs are adjusted based on the coverage selected. Once the plan is purchased, the benefit amounts are fixed for such consumer and the consumer can see, for each health care service from each provider, an estimated credit or debit received for purchasing the health care service from that provider. If the cost for purchasing the health care service from a provider is greater than the benefit amount, the consumer will be debited the difference if the consumer purchases the health care service from that provider. If the cost of purchasing the health care service from a provider is below the benefit amount, the consumer will receive a credit for purchasing the health care service from that provider. The credit can be applied to the consumer's account for payment of premium costs, for covering a future co-pay cost, be refunded to the consumer in cash, and so forth.

The payment processing engine 220 receives the cash rate cost data 262 and the coverage data 272 from the databases 230 and 240, and determines the benefit amount for the purchase. The benefit amount is based on the cash rate data 268 and the coverage data 272. For example, if the cash rate for a health care service is $100, the benefit amount can be set to $70 for a "low" coverage level, $80 for a "medium" coverage level, $90 for a "high" coverage level, and $100 for a "maximum" coverage level. If the cash rate for the health care service is $200, the benefit amounts can be $140, $160, $180, and $200, respectively. In other words, the benefit amount can be a function of the cash rate of a health care service, and then adjusted up or down based on the coverage level purchased by the consumer.

This fixed indemnity allows the consumer to determine in advance of a purchase of a health care service what the credit or debit will be for that purchase. For example, the data processing system 250 can determine that the cash rate for a health care service is $100, and report this to the consumer on the client device 100. The consumer can view the estimated costs for particular instances of the health care service from different health care service providers on the user interface. For example, a first doctor may charge $90 for the health care service, while the cash rate cost is determined by the data processing device 120 to be $100. If the consumer purchases this instance of the health care service with full coverage, the consumer receives a $10 credit because the benefit amount of $100 exceeds the cost paid of $90 at the point of sale. However, if a second doctor provides the health care service for $110, the consumer with full coverage will receive a $10 debit if he purchases the service from the second doctor, because the benefit amount of $100 is less than the cost $110 paid a the point of sale. The notice of debit or credit is sent by alert data 274 to the client device. The alert data can include a phone call, email, push notification, and so forth. In some implementations, the alert data 274 is associated with the smartphone application installed on the client device 110.

Once the benefit is applied by the payment processing engine 220, the insurance payment data 256 is sent to the validation engine 210. The insurance payment data 256 can include the debit or credit data that is used to update the consumer's profile. The validation engine 210 can act as an interface for transmitting the alert data 274 including the credit or debit to the client device 110.

Figure 3:
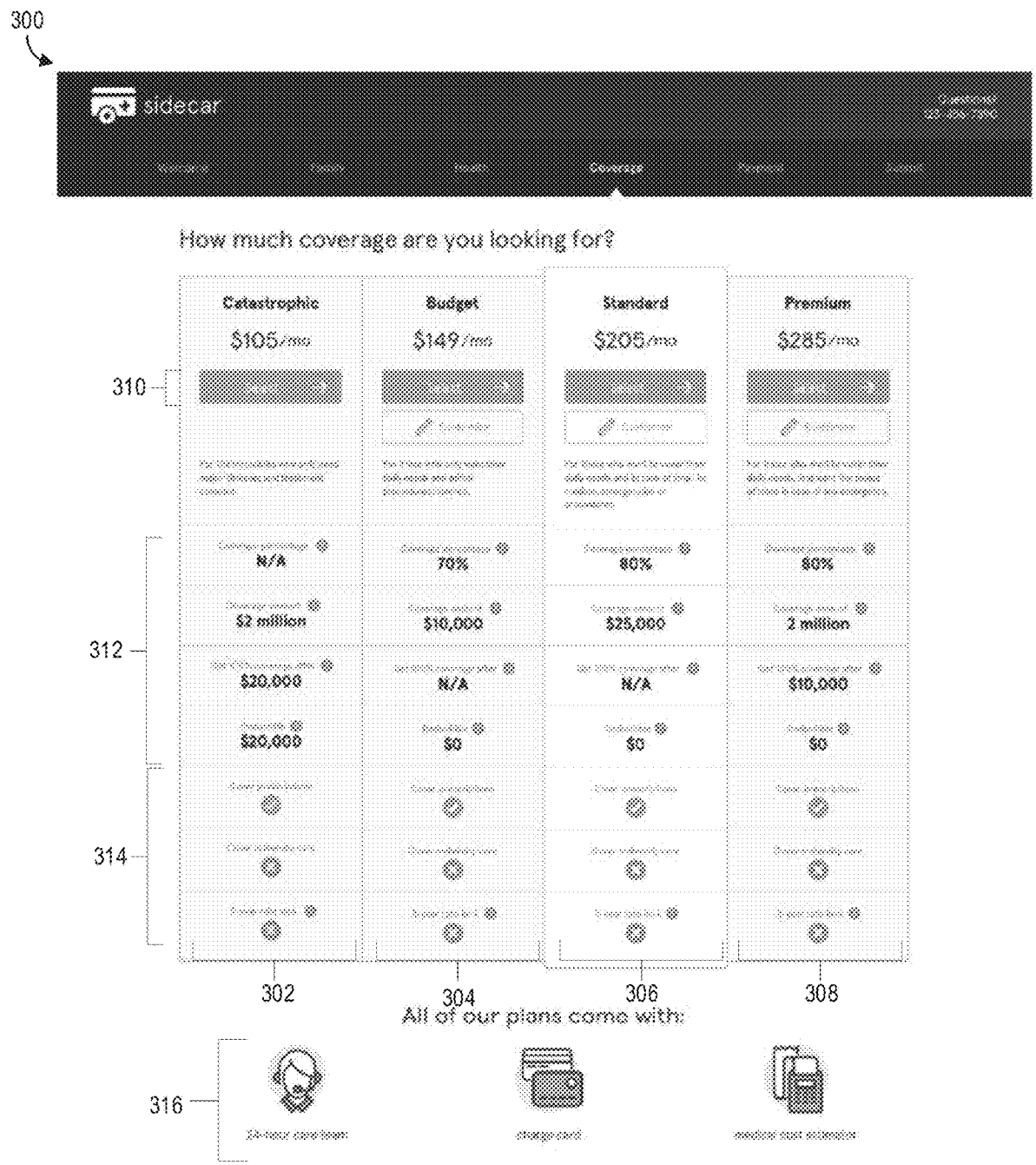

FIG. 3 shows an example user interface 300. The user interface can be presented on client device 110. The user interface 300 shows examples of different levels of coverage that can be selected by the consumer, as previously described. The user interface 300 shows four coverage levels. The four levels shown include a catastrophic coverage level ($105 per month) 302, a budget coverage level 304 ($149 per month), a standard coverage level 306 ($205 per month), and a premium coverage level 308 ($285 per month). Consumers can choose one of these packages and sign up for the benefits as they are presented, or they can choose to customize various parts of the plan. For those who choose to customize a package, they can use a dashboard 400 as shown in FIG. 4.

As stated in relation to FIG. 2, the coverage level selected can determine how much of a fixed benefit amount is paid for a given health care service. This can be shown as a function of the cash rate for the health care service. For example, the user interface includes the coverage level data 312 which shows the benefit amount as a percentage of the cash rate for a health care service. The coverage level data 312 shows premium amounts, deductible amounts, etc. Features data 314 shows what features are covered by the coverage levels 302, 304, 306, and 308, such as whether prescription drugs are covered, whether maternity care is covered, how long a premium rate lock will be, and so forth. The features 314 shown are examples and not an exhaustive list.

One or more controls 310 allow the consumer to interact with the user interface 300, such as to select a coverage level. The controls can include buttons, sliders, dials, etc.

Customer features 316 can be shown which apply to any coverage level. The customer features 316 include a 24-hour customer care team, a charge card (e.g., the card described in relation to FIGS. 1-2), and a medical cost estimator applet.

Figure 4A:
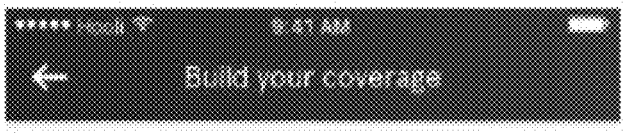
Figure 4B:

FIGS. 4A-4B show example screenshots 400 and 410 of a user interface including a Dashboard Screen. The dashboard can be from a mobile application running on a smartphone or the like. From the dashboard screen, the consumer can input data for selecting an insurance plan. The dashboard screen of screenshots 400 and 410 is comprised of five (5) different sections. The first section represents a coverage percentage 402. The second section represents a coverage amount 404. The third section represents a deductible amount 406. The fourth section represents an additional coverage amount 408, and the fifth section represents a monthly cost of membership 410. The sections are customizable to show data based on a consumer preference. The first section 402 enables the consumer to increase or decrease their co-insurance amount by, for example, moving a control on a slider left or right. The percentage the consumer chooses is the amount of the cash rate for the health care service that the insurance account pays. The consumer pays the remaining amount as a co-pay (e.g., a payment at the point of sale from the consumer's personal account). In the exemplary embodiment shown FIG. 4A, the insurance plan pays 65% of the cash rate for the health care services purchased by the consumer. The consumer is responsible for the remaining 35% of the cost at the time of the transaction (e.g., in cash, with a credit card, etc.). The consumer can choose a lower percentage of coverage to decrease their monthly cost of membership (e.g., a monthly premium).

The second section 404, representing the coverage amount, enables the consumer to choose the maximum amount their insurance plan will pay each year toward their medical costs by, for example, moving a slider to the left or to the right. Once the insurance plan has paid the total amount of cash rate costs of health care services purchased by the consumer, the account is exhausted, and the consumer is responsible for paying 100% of their medical bills thereafter. The consumer can choose a lower annual maximum to decrease their monthly cost of membership.

The third section 406, representing the deductible, enables the consumer to add a deductible to their plan. Adding a deductible will enable the consumer to lower their monthly cost of membership, although they must pay the deductible amount in medical expenses before their health coverage begins to pay any portion.

The fourth section 408, representing additional coverage, enables the consumer to choose whether they would like to add certain types of coverage to their plan by clicking on a button associated with the coverage and sliding the switch to activate or deactivate the coverage. The consumer can activate various add-on coverage, such as prescriptions, maternity care, and a three-year premium rate lock. This concept enables consumers to decrease their monthly cost of membership if they feel they will not benefit from having one or more of these types of coverages, or if their monthly budget does not allow for it.

The fifth section 410, representing the monthly cost of membership (e.g., the monthly premium), shows the consumer their monthly cost of membership based on the parameters they choose for their plan in the sections above. The monthly cost will increase or decrease automatically based on any changes that are made in the previous sections.

As stated previously, the insurance coverage provided according to the exemplary embodiments of the data processing system is designed as comprehensive fixed indemnity. The fixed indemnity model works in that members enrolled in such a plan receive a set amount of reimbursement per health care service, which they typically know ahead of time.

Generally, traditional fixed indemnity health plans only cover a small set of health events such as hospital admission or critical illness (i.e., cancer). Conversely, the plan of the data processing system can cover every medically necessary procedure. This is because the data processing system can access or estimate closely the cash rate cost for health care services and also simulate cash rate purchases from the perspective of the health care service providers. The insurance plan can thus cover almost any health care service from almost any provider under one plan.

To enable consumers to quickly and easily find the fixed benefit amount for a particular health care service, a software module that permits consumers to search for medical services, prescription medications, etc., and see the exact amount that is covered under their plan. In some implementations, as long as there is medical billing code associated with the service or prescription, the software module can present the covered amount.

Figure 5:
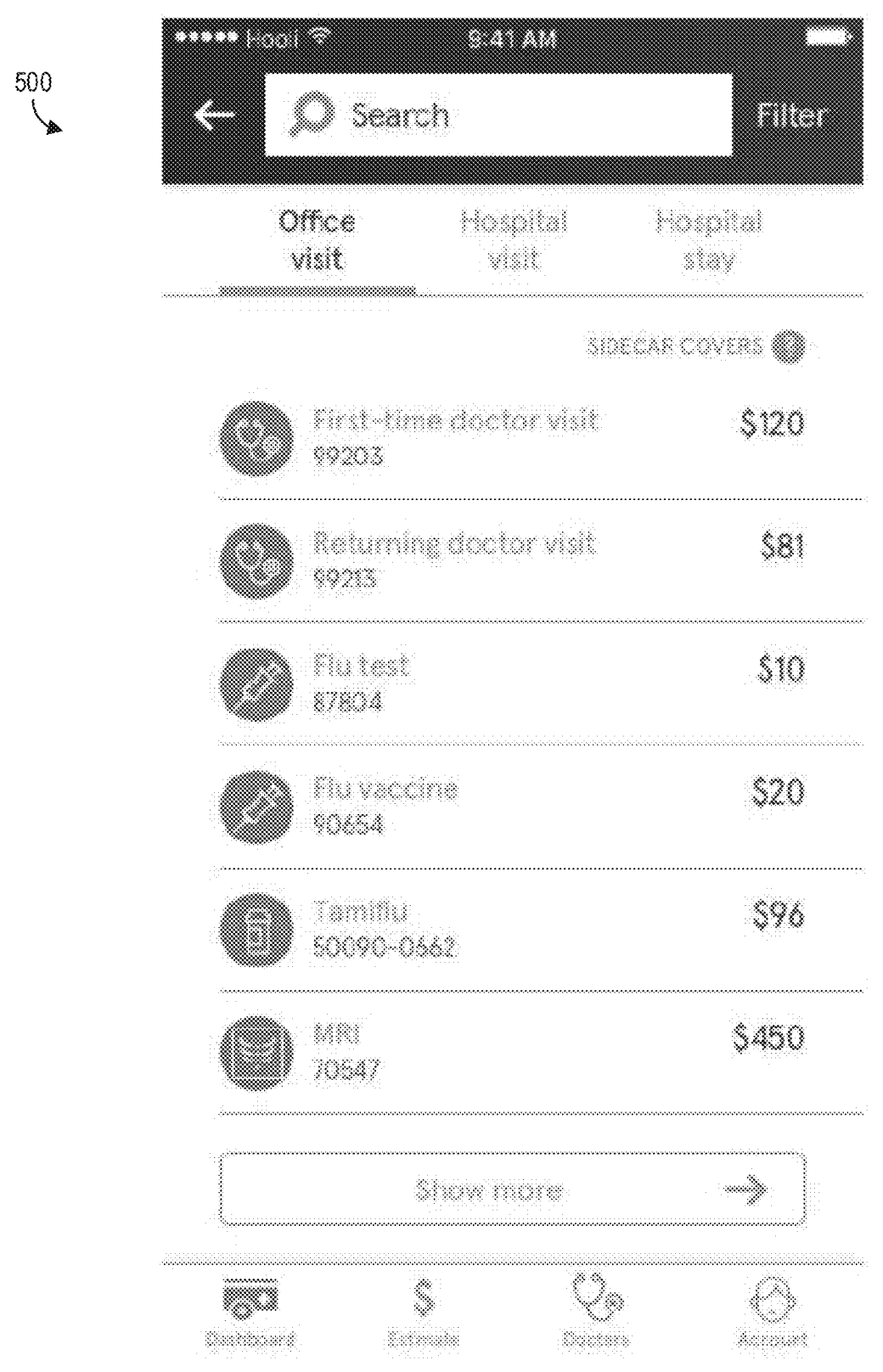

FIG. 5 shows an exemplary screenshot 500 of a coverage screen from a mobile application running on a smartphone or the like. A first-time doctor visit, for example, is covered up to $120. Similarly, a flu vaccine is covered up to $20, and a magnetic resonance imaging (MRI) scan is covered up to $450. The coverage screen 500 allows the user to determine, before making an appointment with a medical service provider, exactly what is covered. This information, combined with the health care service provider's cash rate, helps the consumer select a health care service provider. As stated above, the cash rate is the amount that the health care service provider charges to an individual who does not have traditional health care coverage, and who is paying cash for the health care service. For example, if a consumer is selecting among three (3) different doctors for a first-time office visit. Doctor A charges a cash payment rate of $200 for a for a first-time office visit, doctor B charges $120, and doctor C charges $100. The data processing device 120 can show to the user this data in advance of a purchase. By knowing in advance that the plan will cover up to $120, the consumer can either choose to pay the extra for doctor A, or pay nothing to see doctor B, or receive a credit up to $20 to see doctor C.

However, the consumer often has well more than three (3) doctors from which to choose. To make it easy for consumers to find doctors in their area that best fit their budget, the data processing system permits consumers to search for medical service providers in their area, and compare out-of-pocket costs for each medical service provider, for a particular service. As in the example above, once the consumer knows the coverage amount and the medical service provider cash payment rate, they can make an informed decision.

Figure 6A:
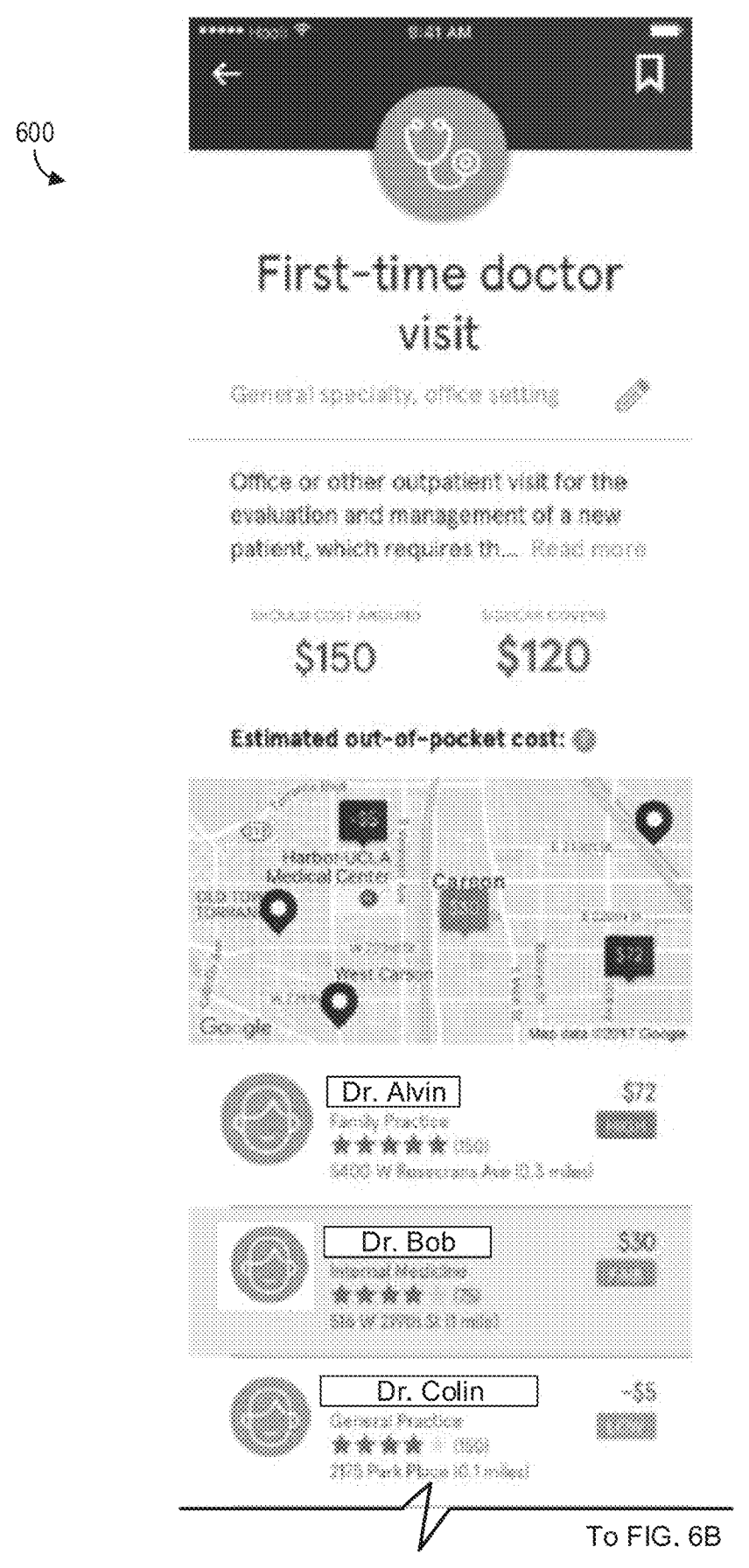
Figure 6B:
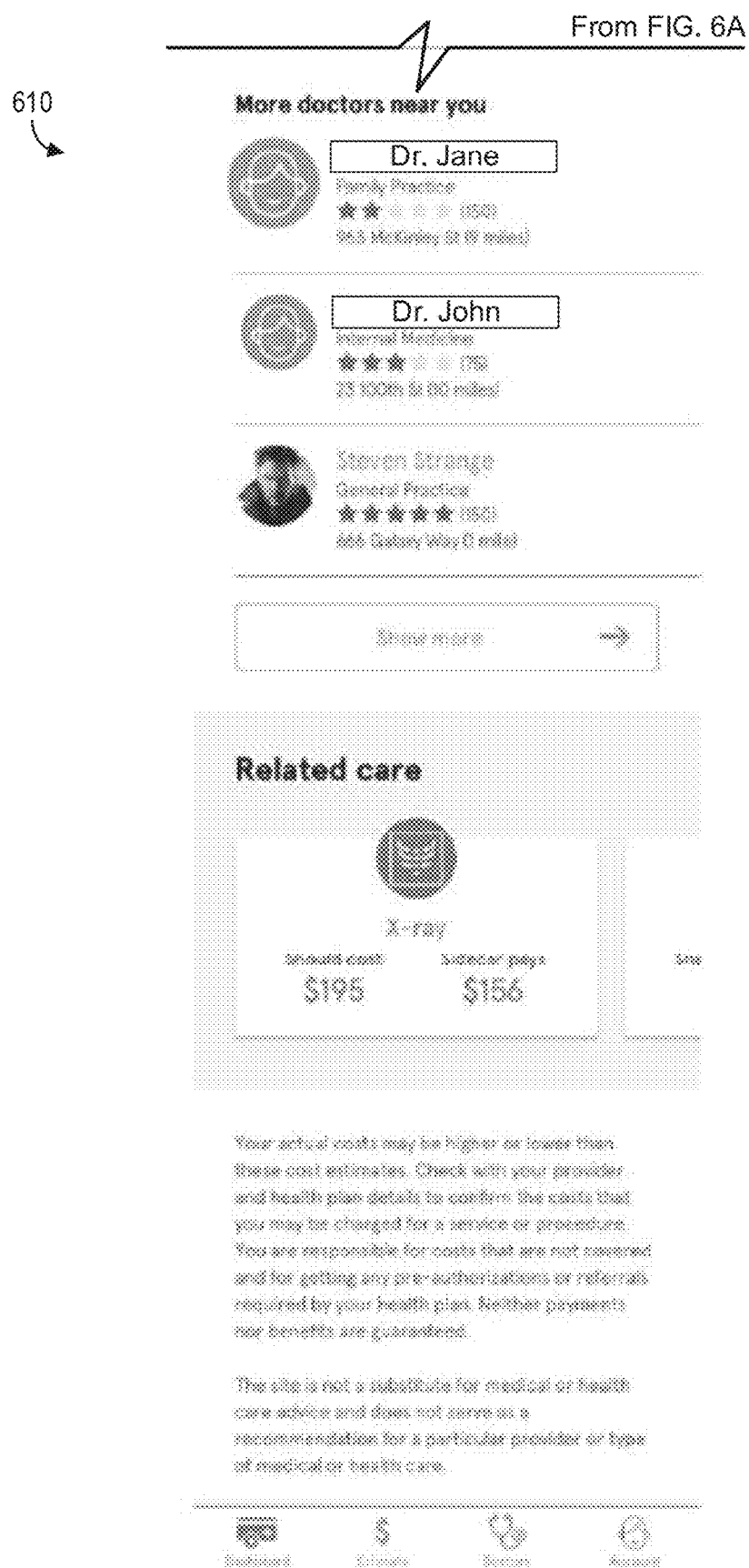

FIGS. 6A-6B show example screenshots 600 and 610 of a services search screen from a mobile application for the client device 110. A first-time doctor visit, for example, ranges from $115 to $192 in the local area being searched. Since the plan covers up to $120, the consumer is presented with the names of local doctors, and the corresponding out-of-pocket expense associated with the service. For example, Dr. Alvin charges $192 for a first-time visit. The consumer must then pay the difference over $120, or $72. Dr. Bob charges $150, so the consumer pays only $30 out-of-pocket for the visit. Dr. Colin charges $115, so the consumer is shown a negative value (−$5). If the consumer selects a particular doctor, they are shown a doctor detail screen with additional information, including the cash payment rates for other services.

The data processing device 120 generates the cash payment information for each medical service and medical service provider through user input, or crowdsourcing. For example, the cash rate for a particular doctor may be entered into the system by the doctor themselves, or by the patient. The next patient is shown exactly what that doctor charges for the health care service in question, without having to ask. Once the database (e.g., data storage 160 of FIG. 1 or health care service database 230 of FIG. 2) of cash rates includes values for each health care service, the data processing device 120 can cause the user interface to show to a consumer the price health care service provider charges for a specific service. This, in turn, assists the consumer in making an informed selection of a health care service provider.

FIG. 6B shows a user interface 610 that includes details as to what a cash rate for a particular health care service provider is relative to other providers of the health care service in the market (e.g., a geographic region). The interface 610 enables consumers to share doctor reviews about their experience (using for example, a 1 Star to 5 Star rating system).

Figure 7:
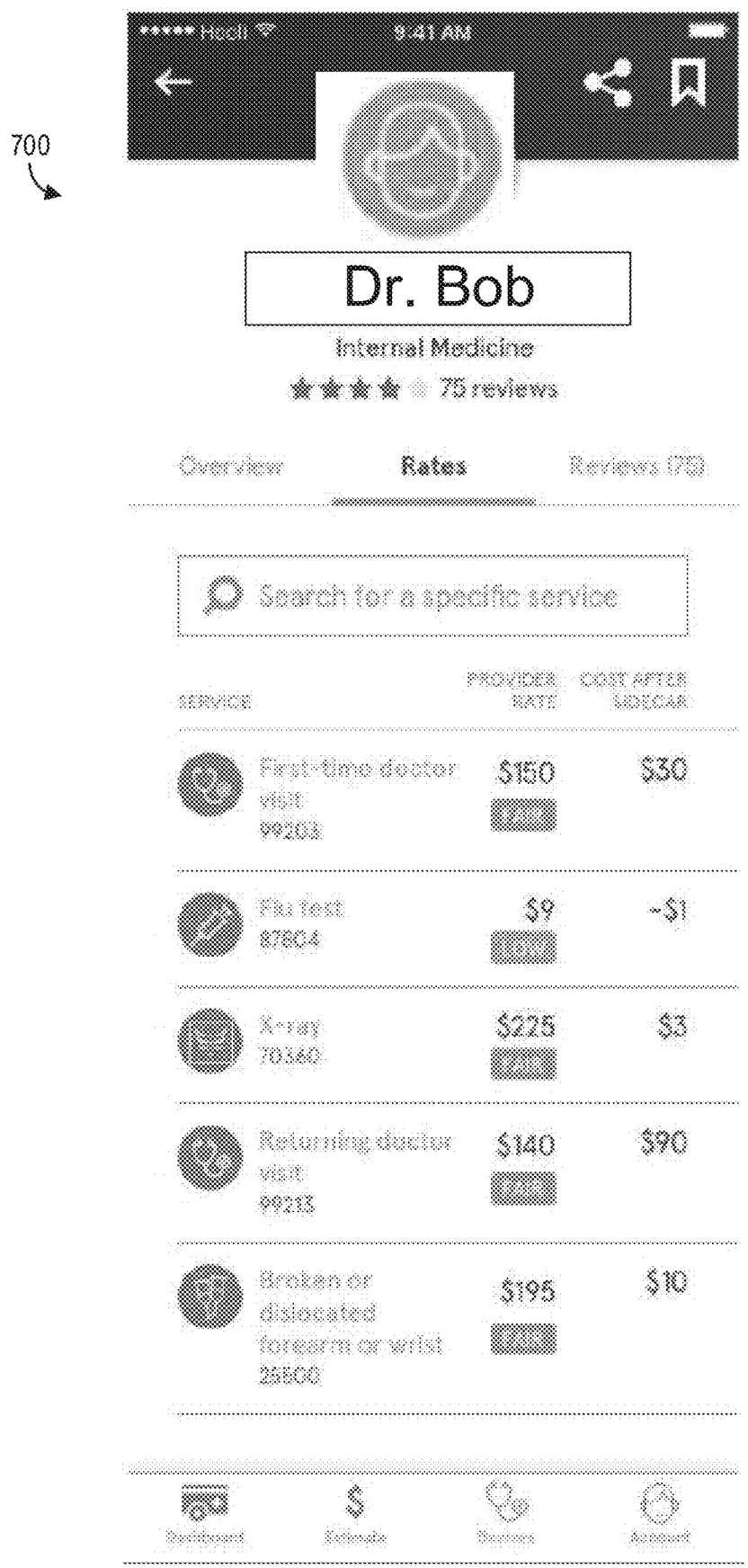

FIG. 7 shows an example screenshot 700 of a doctor detail screen from a mobile application of the client device. The doctor detail screen shows detailed information about the doctor and their services. This information may include reviews left about the health care service provider from other consumers, and the health care service provider's rates for various common services. The user interface 700 provides the ability to search for a particular service. The system also automatically calculates what the consumer's co-pay (e.g., out of pocket) cost is for each health care service based on the insurance plan coverage and cash rate cost for the health care service provider. The information is presented on the doctor detail screen 700.

The data processing device 120 includes a payment system using a payment card as described above. A charge card is provided to the consumer. The card is much like a traditional credit or debit card, but which is not necessarily backed by lending institution. Participants use the charge card to pay for procedures at the point when they receive those health care services, or before the health care service is provided, depending on the provider's protocol. With a single transaction activated by a card swipe by the provider, the plan operator validates coverage and enacts backend transactions, as described in relation to FIG. 2, for covering the cost from each of the consumer's account and the insurance account. As previously stated, these transactions occur in real time or near real time, so from the perspective of both the plan participant and the medical services provider, payment is virtually instantaneous. For example, for a purchase from Dr. Bob above for a first time office visit costing $150, the consumer swipes the charge card. This transaction deducts $30 from the consumer's associated payment account (e.g., a personal checking account or credit card account). The remaining $120 is deducted from the insurance plan operator's account. Dr. Bob is paid the $150 she charges for a cash-payment for a first time visit. The mobile application software creates an expense record whenever services are provided and a transaction is generated by a swipe of the payment card.

Figure 8:
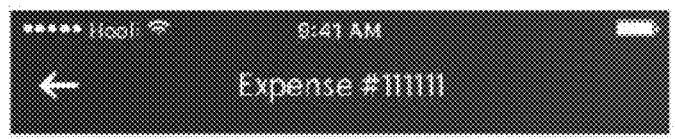

FIG. 8 shows an example screenshot 800 of an expense screen from a mobile application running on a Smartphone or the like. The expense screen 800 shows detailed information about the health care services provided, the plan coverage, and the consumer's out-of-pocket cost. The consumer may also use the camera on their smartphone to take a photograph of any receipt they are provided by the doctor, and upload that image to the system for verification purposes.

The debit or credit to the consumer's account can occur after the transaction data are processed. For example, the data representing the actual cash cost paid by the consumer (e.g., the photograph of the invoice) can be provided by the consumer after the health care service has been received. The consumer can provide the photograph minutes, days, months, etc. after the transaction (e.g., a card swipe) to the data processing device 120. The data processing device 120 can "true-up" the consumer's account based on this data. If a consumer does not upload data showing the actual cost paid to the health care service provider, a reminder can be sent to the client device 110.

Figure 9:
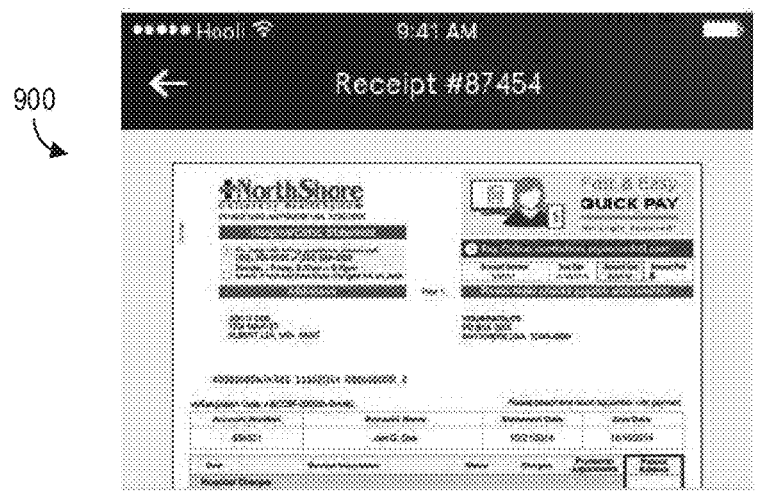
Figure 9:
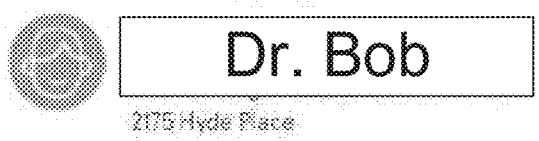
Figure 9:

FIG. 9 is an example screenshot 900 of a receipt upload screen from the mobile application running the client device 110. The data processing device 120, using this image data of the receipt, can more easily adjudicate the claim. For example, the data processing device 120 can scan the image and parse the costs and types of health care services provided. The data processing device 120 can automatically calculate any refund the consumer is due from the preliminary charge, or any incremental amount that is due by the consumer. The consumer then receives the refund or pays the incremental amount by the client device 110 with the application. From the perspective of the health care service provider, the plan operator does not exist. The health care service provider is simply paid their cash payment rate.

As discussed previously, the data processing device 120 be carried out as a mobile application (App) running on one or more computing devices (e.g., smart phone, PC, server-client devices), or alternatively within a web browser running one or more computing devices (e.g., PC). In either case, the method allows consumers to: (1) select health plan coverage; (2) search for medical procedure covered costs, (3) search for doctor/medical service provider costs, (4)

select a doctor/medical service provider based on relative costs, and (5) submit a claim which is immediately processed.

Figure 10:
FIGS. 10-11 show flow diagrams each including an example process for processing network data records transmitted from a plurality of remote, distributed terminal devices.

FIG. 10 shows a flow diagram of an example process 1000 for processing network data records transmitted from a plurality of remote, distributed terminal devices. The data processing system previously described is configured to receive (1002), over a payment processing network, a request requesting payment for a health care service and a key that uniquely identifies a consumer of health care services. The data processing system is configured to process (1004) in near real-time with respect to when the request is received and through a payment network, cash payment of the health care service. The data processing system is configured to access (1006), from a hardware storage device, a node labeled with the key. The node can represent a data record that refers to a consumer profile. The key can include a consumer identifier that identifies the consumer. The data processing system is configured to look up (1008), in the accessed node, coverage data that specifies an amount of the health care service paid by a health insurance provider of the payment network and an amount paid by the consumer, wherein the amount paid by the health insurance provider is a specified amount of a determined market price of the health care service.

Figure 11:
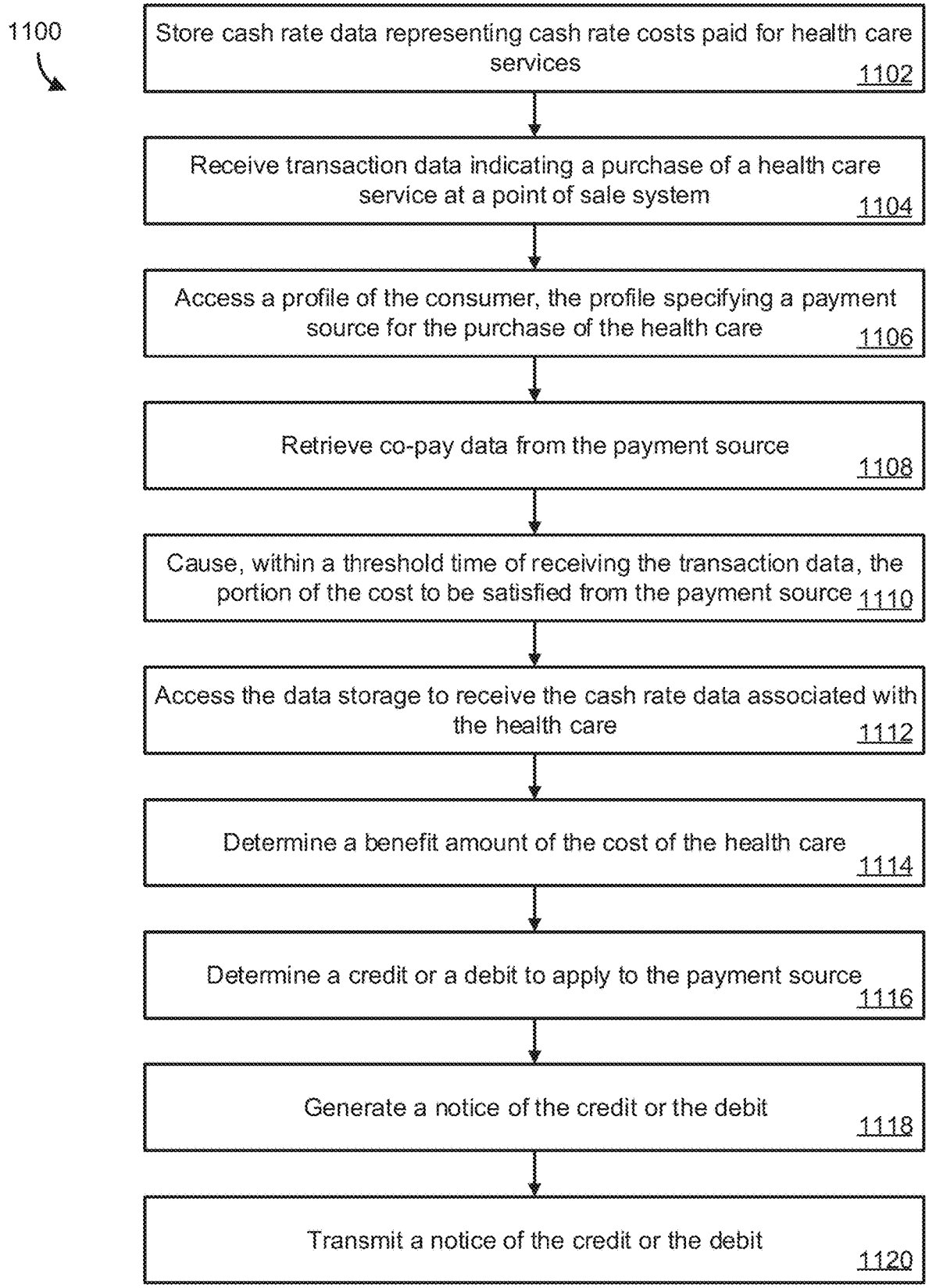

FIG. 11 shows a flow diagram of an example process 1100 for processing network data records transmitted from a plurality of remote, distributed terminal devices. The data processing system is configured to process a cash payment for a health care service that is at least partly covered by a health insurance provider. The data processing system is configured to store (1102), by a data storage, cash rate data representing cash rate costs paid for health care services for each of a plurality of transactions processed by point of sale systems of health care providers. The data processing system is configured to receive (1104), by a payment processing engine, transaction data indicating a purchase of a health care service at a point of sale system of a health care provider using a payment card identifying a consumer of the health care. The data processing system, in response to receiving the transaction data, accesses (1106) a profile of the consumer, the profile specifying a payment source for the purchase of the health care. The data processing system retrieves (1108) co-pay data from the payment source, the co-pay data specifying a portion of a cost of the health care being paid by the payment source. The data processing system causes (1110), within a threshold time of receiving the transaction data, the portion of the cost to be satisfied from the payment source and a remaining portion of the cost to be satisfied from a coverage account. The data processing system accesses (1112), by the payment processing engine, the data storage to receive the cash rate data associated with the health care. The data processing system determines (1114), by the payment processing engine, a benefit amount of the cost of the health care, the benefit amount of the cost being based on the cash rate costs paid for the health care. The data processing system determines (1116), by the payment processing engine, a credit or a debit to apply to the payment source by comparing the benefit amount of the cost to the remaining portion of the cost satisfied by the coverage account. The data processing system generates (1118) a notice of the credit or the debit. The data processing system causes (1120) transmission of the notice to a computing device associated with the consumer.

Some implementations of subject matter and operations described in this specification can be implemented in digital electronic circuitry, or in computer software, firmware, or hardware, including the structures disclosed in this specification and their structural equivalents, or in combinations of one or more of them. For example, in some implementations, the data processing device 120, the client device 110, and the terminal devices 140 can be implemented using digital electronic circuitry, or in computer software, firmware, or hardware, or in combinations of one or more of them. In another example, the process 1000 or 1100 can be implemented using digital electronic circuitry, or in computer software, firmware, or hardware, or in combinations of one or more of them.

Some implementations described in this specification (e.g., the payment processing engine 220, the validation engine 210, etc.) can be implemented as one or more groups or modules of digital electronic circuitry, computer software, firmware, or hardware, or in combinations of one or more of them. Although different modules can be used, each module need not be distinct, and multiple modules can be implemented on the same digital electronic circuitry, computer software, firmware, or hardware, or combination thereof.

Some implementations described in this specification can be implemented as one or more computer programs, i.e., one or more modules of computer program instructions, encoded on computer storage medium for execution by, or to control the operation of, data processing apparatus. A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The term "data processing apparatus" encompasses all kinds of apparatus, devices, and machines for processing data, including by way of example a programmable processor, a computer, a system on a chip, or multiple ones, or combinations, of the foregoing. In some implementations, the query response module 104 and/or the data structure module 106 comprises a data processing apparatus as described herein. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communication network.

Some of the processes and logic flows described in this specification can be performed by one or more programmable processors executing one or more computer programs to perform actions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and processors of any kind of digital computer. Generally, a processor will receive instructions and data from a read only memory or a random access memory or both. A computer includes a processor for performing actions in accordance with instructions and one or more memory devices for storing instructions and data. A computer may also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non-volatile memory, media and memory devices, including by way of example semiconductor memory devices (e.g., EPROM, EEPROM, flash memory devices, and others), magnetic disks (e.g., internal hard disks, removable disks, and others), magneto optical disks, and CD-ROM and DVD-ROM disks. The processor and the memory can be supplemented by, or incorporated in, special purpose logic circuitry.

To provide for interaction with a user, operations can be implemented on a computer having a display device (e.g., a monitor, or another type of display device) for displaying information to the user and a keyboard and a pointing device (e.g., a mouse, a trackball, a tablet, a touch sensitive screen, or another type of pointing device) by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). A relationship of client and server may arise by virtue of computer programs running on the respective computers and having a client-server relationship to each other.

Figure 12:
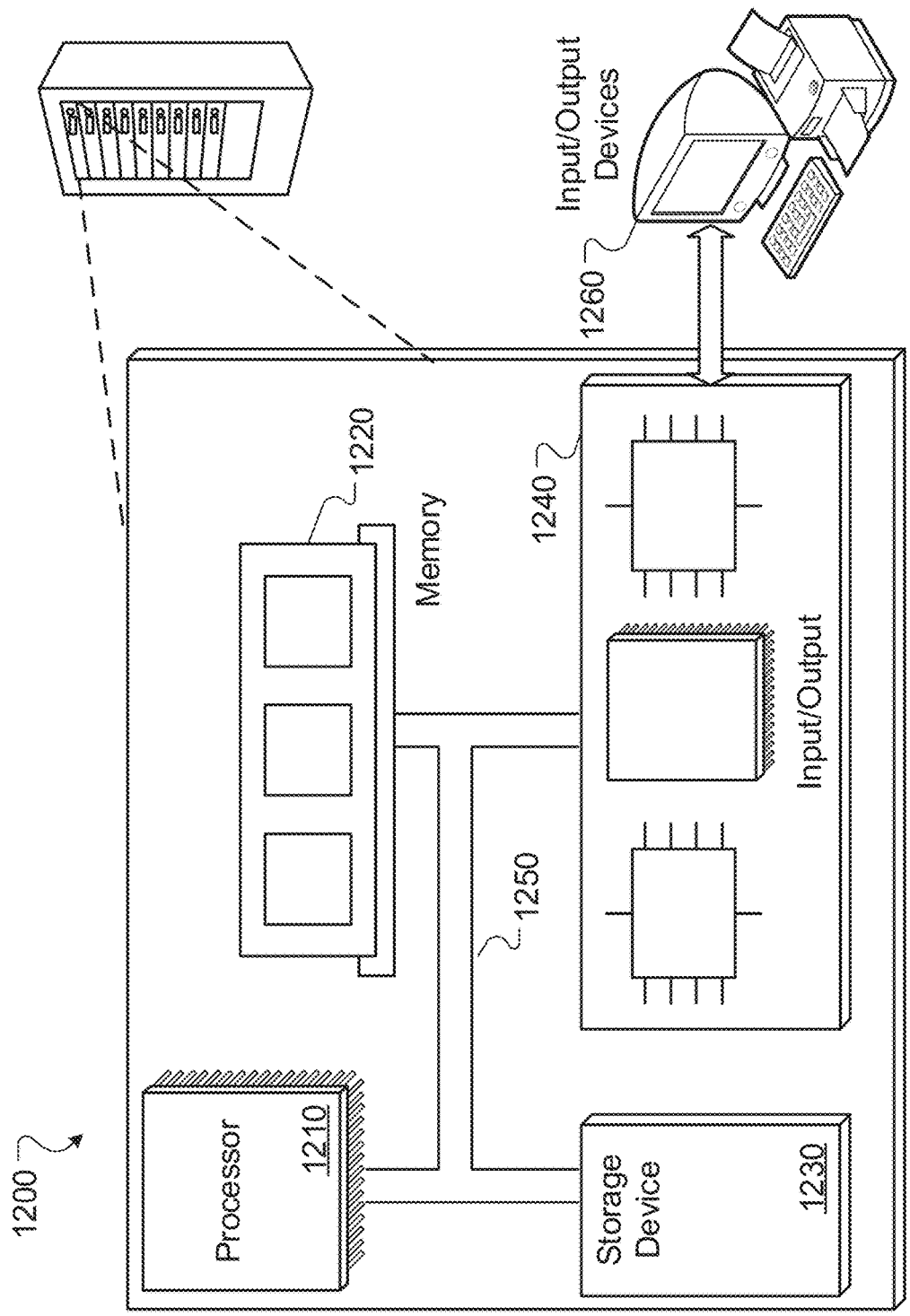
FIG. 12 is a diagram of an example computing system.

FIG. 12 shows an example computer system 1200 that includes a processor 1210, a memory 1220, a storage device 1230 and an input/output device 1240. Each of the components 1210, 1220, 1230 and 1240 can be interconnected, for example, by a system bus 1250. The processor 1210 is capable of processing instructions for execution within the system 1200. In some implementations, the processor 1210 is a single-threaded processor, a multi-threaded processor, or another type of processor. The processor 1210 is capable of processing instructions stored in the memory 1220 or on the storage device 1230. The memory 1220 and the storage device 1230 can store information within the system 1200.

The input/output device 1240 provides input/output operations for the system 1200. In some implementations, the input/output device 1240 can include one or more of a network interface device, e.g., an Ethernet card, a serial communication device, e.g., an RS-232 port, and/or a wireless interface device, e.g., an 802.11 card, a 3G wireless modem, a 4G wireless modem, a 5G wireless modem, etc. In some implementations, the input/output device can include driver devices configured to receive input data and send output data to other input/output devices, e.g., keyboard, printer and display devices 1260. In some implementations, mobile computing devices, mobile communication devices, and other devices can be used.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, it will be understood that various modifications may be made without departing from the spirit and scope of the data processing system described herein. Accordingly, other embodiments are within the scope of the following claims.

What is claimed is:

1. A data processing system, configured to process a payment for a health care service that is at least partly covered by a health insurance provider, the data processing system comprising:
   a data storage configured to:
      store cash rate data representing cash rate costs paid for health care services for each of a plurality of transactions processed by point of sale systems of health care providers;
   a payment processing engine comprising one or more processors, the payment processing engine configured to:
      receive transaction data indicating a purchase of a health care service at a point of sale system of a health care provider, the transaction data specifying a key value that uniquely identifies a consumer of the health care service;
      in response to receiving the transaction data, access, from a hardware storage device, a node labeled with the key value;
      looking-up, in the accessed node, coverage data of the consumer, with the coverage data specifying a payment source for the purchase of the health care;
      retrieve co-pay data from the payment source, the co-pay data specifying a portion of a cost of the health care being paid by the payment source;
      cause, within a threshold time of receiving the transaction data, the portion of the cost to be satisfied from the payment source and a remaining portion of the cost to be satisfied from a coverage account;
      access the data storage to receive the cash rate data associated with the health care;

determine a benefit amount of the cost of the health care, the benefit amount of the cost being based on the cash rate costs paid for the health care;

determine a credit or a debit to apply to the payment source by comparing the benefit amount of the cost to the remaining portion of the cost satisfied by the coverage account;

generate a notice of the credit or the debit; and cause transmission of the notice to a computing device associated with the consumer.

2. The data processing system of claim 1, wherein the payment processing engine is further configured to update the cash rate data associated with the health care in response to receiving the transaction data.

3. The data processing system of claim 1, wherein the cash rate data comprises, for each health care, a weighted average of a cost for each instance of purchasing the health care in the plurality of transactions.

4. The data processing system of claim 1, wherein the data storage comprises different cash rate data for each geographic region of a plurality of geographic regions associated with the plurality of transactions.

5. The data processing system of claim 1, wherein the benefit amount is adjusted based on one or more demographics of the consumer represented in a profile of the consumer.

6. The data processing system of claim 1, wherein the benefit amount is adjusted based on a cost coverage setting of a profile of the consumer.

7. The data processing system of claim 1, wherein the transaction data comprises an identifier representing the health care service.

8. The data processing system of claim 7, wherein the identifier can be mapped to various standard medical codes.

9. The data processing system of claim 1, wherein receiving the transaction data comprises:
   requesting validation data for the point of sale system as being associated with an approved health care provider; and
   in response to receiving the validation data indicating that the health care is approved, enabling the remaining portion of the cost to be satisfied from the coverage account.

10. The data processing system of claim 1, wherein causing, within the threshold time of receiving the transaction data, the portion of the cost to be satisfied from the payment source and the remaining portion of the cost to be satisfied from the coverage account, satisfies a timeout function of the point of sale system for the purchase of a health care.

11. The data processing system of claim 1, further comprising a user interface engine configured to generate presentation data for presenting the notice of the credit or the debit on the computing device associated with the consumer.

12. The data processing system of claim 11, wherein the presentation data comprises a push notification or alert.

13. The data processing system of claim 11, wherein the presentation data comprises the benefit amount for each transaction associated with the consumer.

14. The data processing system of claim 13, wherein the presentation data is configured to be searchable based on the benefit amount.

15. The data processing system of claim 11, wherein the payment processing engine is configured to generate additional cost data representing a projected cost or credit associated with each of the plurality of transactions, the projected cost or credit being a function of the cash rate data for each of the transactions of the plurality; and
   wherein the presentation data comprises a representation of the additional cost data.

16. The data processing system of claim 1, wherein determining the credit or the debit to apply to the payment source comprises:
   receiving image data representing a medical invoice including the cost for purchasing the health care service;
   extracting the cost from the image data; and
   verifying that the cost of the transaction data matches the extracted cost from the image data, wherein determining the credit or the debit to apply to the payment source comprises comparing the extracted cost to the benefit amount.

17. A method for processing a payment for a health care service that is at least partly covered by a health insurance provider, the method comprising:
   storing cash rate data representing cash rate costs paid for health care services for each of a plurality of transactions processed by point of sale systems of health care providers;
   receiving transaction data indicating a purchase of a health care service at a point of sale system of a health care provider, the transaction data specifying a key value that uniquely identifies a consumer of the health care;
   in response to receiving the transaction data, accessing, from a hardware storage device, a node labeled with the key value;
   looking-up, in the accessed node, coverage data of the consumer, with the coverage data specifying a payment source for the purchase of the health care;
   retrieving co-pay data from the payment source, the co-pay data specifying a portion of a cost of the health care being paid by the payment source;
   causing, within a threshold time of receiving the transaction data, the portion of the cost to be satisfied from the payment source and a remaining portion of the cost to be satisfied from a coverage account;
   accessing a data storage to receive the cash rate data associated with the health care;
   determining a benefit amount of the cost of the health care, the benefit amount of the cost being based on the cash rate costs paid for the health care;
   determining a credit or a debit to apply to the payment source by comparing the benefit amount of the cost to the remaining portion of the cost satisfied by the coverage account;
   generating a notice of the credit or the debit; and
   causing transmission of the notice to a computing device associated with the consumer.

18. The method of claim 17, wherein receiving the transaction data comprises:
   requesting validation data for the point of sale system as being associated with an approved health care provider; and
   in response to receiving the validation data indicating that the health care is approved, enabling the remaining portion of the cost to be satisfied from the coverage account.

19. The method of claim 17, wherein causing, within the threshold time of receiving the transaction data, the portion of the cost to be satisfied from the payment source and the remaining portion of the cost to be satisfied from the coverage account, satisfies a timeout function of the point of sale system for the purchase of a health care.

20. The method of claim 17, wherein determining the credit or the debit to apply to the payment source comprises:
receiving image data representing a medical invoice including the cost for purchasing the health care service;
extracting the cost from the image data; and
verifying that the cost of the transaction data matches the extracted cost from the image data, wherein determining the credit or the debit to apply to the payment source comprises comparing the extracted cost to the benefit amount.

21. One or more non-transitory computer readable media storing instructions for processing a payment for a health care service that is at least partly covered by a health insurance provider, the instructions configured to cause at one processor executing the instructions to perform operations comprising:
storing cash rate data representing cash rate costs paid for health care services for each of a plurality of transactions processed by point of sale systems of health care providers;
receiving transaction data indicating a purchase of a health care service at a point of sale system of a health care provider, the transaction data specifying a key value that uniquely identifies a consumer of the health care;
in response to receiving the transaction data, accessing, from a hardware storage device, a node labeled with the key value;
looking-up, in the accessed node, coverage data of the consumer, with the coverage data specifying a payment source for the purchase of the health care;
retrieving co-pay data from the payment source, the co-pay data specifying a portion of a cost of the health care being paid by the payment source;
causing, within a threshold time of receiving the transaction data, the portion of the cost to be satisfied from the payment source and a remaining portion of the cost to be satisfied from a coverage account;
accessing a data storage to receive the cash rate data associated with the health care;
determining a benefit amount of the cost of the health care, the benefit amount of the cost being based on the cash rate costs paid for the health care;
determining a credit or a debit to apply to the payment source by comparing the benefit amount of the cost to the remaining portion of the cost satisfied by the coverage account;
generating a notice of the credit or the debit; and
causing transmission of the notice to a computing device associated with the consumer.

22. The one or more non-transitory computer readable media of claim 21, wherein receiving the transaction data comprises:
requesting validation data for the point of sale system as being associated with an approved health care provider; and
in response to receiving the validation data indicating that the health care is approved, enabling the remaining portion of the cost to be satisfied from the coverage account.

23. The one or more non-transitory computer readable media of claim 21, wherein causing, within the threshold time of receiving the transaction data, the portion of the cost to be satisfied from the payment source and the remaining portion of the cost to be satisfied from the coverage account, satisfies a timeout function of the point of sale system for the purchase of a health care.

24. The one or more non-transitory computer readable media of claim 21, wherein determining the credit or the debit to apply to the payment source comprises:
receiving image data representing a medical invoice including the cost for purchasing the health care service;
extracting the cost from the image data; and
verifying that the cost of the transaction data matches the extracted cost from the image data, wherein determining the credit or the debit to apply to the payment source comprises comparing the extracted cost to the benefit amount.

* * * * *